United States Patent [19]
Friedman et al.

[11] 4,029,671
[45] June 14, 1977

[54] 3-[(5-NITRO-2-IMIDAZOLYL)PYRAZOL-5-YL]OXAMIC ACID DERIVATIVES

[75] Inventors: Henry Friedman; Emily J. Canada, both of Indianapolis, Ind.

[73] Assignee: Eli Lilly and Company, Indianapolis, Ind.

[22] Filed: Mar. 22, 1976

[21] Appl. No.: 668,874

[52] U.S. Cl. .......................... 260/310 R; 260/311; 424/273

[51] Int. Cl.$^2$ ...................... C07D 233/95

[58] Field of Search ............ 260/310, 311; 424/273

[56] References Cited

UNITED STATES PATENTS

| | | | |
|---|---|---|---|
| 3,836,541 | 9/1974 | Johnson et al. | 260/326.2 |
| 3,947,467 | 3/1976 | Verge et al. | 260/310 R |

FOREIGN PATENTS OR APPLICATIONS 2,431,775  2/1975  Germany

OTHER PUBLICATIONS

*Chemical Abstracts,* vol. 83:10079k (1975).

*Primary Examiner*—Donald B. Moyer
*Attorney, Agent, or Firm*—Dwight E. Morrison; Everet F. Smith

[57] ABSTRACT

There are disclosed novel 3-[(5-nitro-2-imidazolyl)-pyrazol-5-yl]oxamic acid derivatives and salts thereof, exhibiting utility as antibacterial, antiprotozoal, and antifungal agents, making the compounds useful particularly in veterinary medicine, especially in controlling bacterial and protozoal infections of cattle, swine, and poultry.

6 Claims, No Drawings

3-[(5-NITRO-2-IMIDAZOLYL)PYRAZOL-5-YL]OXAMIC ACID DERIVATIVES

BACKGROUND OF THE INVENTION

1. Field of the Invention

A great deal of research has been conducted to develop agents for the control of bacterial and protozoal infections of poultry, swine and cattle. Thus, compounds and methods for controlling colibacillosis, pasteurellosis and salmonellosis in cattle, chickens and swine, coccidiosis in chickens, as well as swine dysentery, have been the subject of extended research for many years.

2. Description of the Prior Art

In the prior art, U.S. Pat. No. 3,836,541 (Sept. 17, 1974), teaches 3-cyano-2-pyrryloxamic acids and salts thereof, alleged to be useful in the prophylactic treatment of sensitized humans and mammals for allergic and all anaphylactic reactions of a reagent-mediated and non-reagent-mediated nature. The salts disclosed in this reference are salts of the carboxyl group of the oxamic acid, and include aluminum, ammonium, sodium, potassium, calcium, and tris(hydroxymethyl)-methyl ammonium salts. There is no teaching in the reference of the preparation or possibility of preparation of salts other than the carboxylic acid salts.

The compounds described in the prior art set forth above therefore differ significantly in structure and in utility from those of the instant application.

SUMMARY OF THE INVENTION

This invention relates to novel 3-[(5-nitro-2-imidazolyl)pyrazol-5-yl]oxamic acid derivatives and salts thereof, which are active as antibacterial, antifungal, and antiprotozoal agents, and to methods for the preparation of the compounds. The novel compounds are active in vitro against Pasteurella multocida and E. coli, and are active against Salmonella typhimurium in chicks.

DESCRIPTION OF THE PREFERRED EMBODIMENT

This invention relates to novel substituted oxamic acid derivatives. More particularly, it relates to novel 3-[(5-nitro-2-imidazolyl)pyrazol-5-yl]oxamic acid derivatives and salts thereof of the formulas:

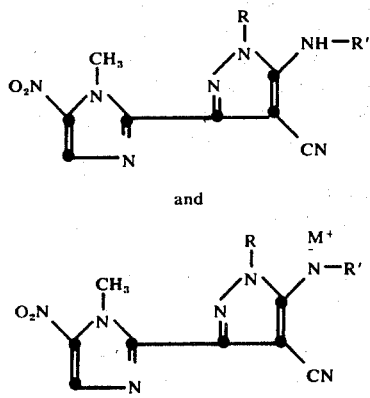

wherein
R is $C_1$–$C_3$ alkyl, halo ($C_1$—$C_3$)alkyl, or hydroxy($C_1$—$C_3$)alkyl;
R' is selected from the group consisting of

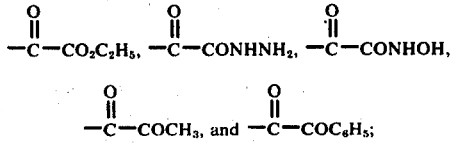

and
M is an ion selected from the group consisting of $Na^+$, $K^+$, $NH_4^+$, and $Li^+$.

Of the compounds disclosed by the above formulas, those which are preferred are of the formulas

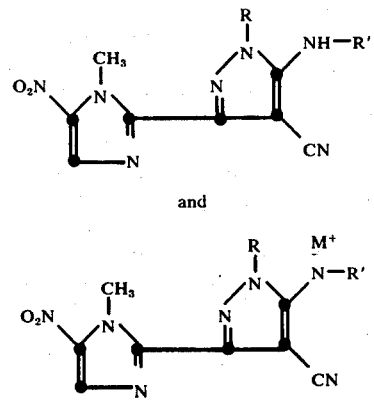

wherein
R is methyl
R' is selected from the group consisting of

and
M is an ion selected from the group consisting of $Na^+$ and $K^+$.

In the above formulas, $C_1$–$C_3$ alkyl represents methyl, ethyl, n-propyl, or isopropyl.

Halo ($C_1$—$C_3$)alkyl represents a halogenated straight or branched-chain saturated hydrocarbon such as halomethyl, 2-haloethyl, 3-halopropyl, 2-halopropyl, and the like, wherein halo is bromo, chloro, iodo, or fluoro.

Hydroxy($C_1$—$C_3$)alkyl represents hydroxymethyl, 2-hydroxyethyl, and 3-hydroxypropyl.

The novel compounds coming within the scope of the generic formula supra have demonstrated in vitro activity against a number of microorganisms, several of which are important animal pathogens:

Pasteurella multocida
 (cattle)
 (turkey)
Escherichia coli
Mycoplasma hyorhinis
Mycoplasma hyopneumoniae
Salmonella dublin
Staphylococcus SP1130
Mycoplasma gallisepticum 38502
Mycoplasma synoviae The novel compounds coming within the scope of the generic formula, supra, are readily snythesized using a 5-amino-1-R-3-(1-methyl-5-nitro-2-imidazolyl)-pyrazole-4-carbonitrile as the starting compound.

The preparation of these starting compounds, used in the synthesis of the novel compounds of this invention, is taught in U.S. Pat. No. 3,947,467 (March 30, 1976).

An exemplary starting compound, 5-amino-1-methyl-3-(1-methyl-5-nitro-2-imidazolyl)pyrazole-4-carbonitrile, is readily synthesized starting from commercially-available 2-methyl-5-nitroimidazole. The 2-methyl-5-nitroimidazole is allowed to react with a suitable alkylating agent, such as dimethyl sulfate, in a suitable solvent, for example benzene, to yield the compound identified as 1,2-dimethyl-5-nitroimidazole. This latter compound is in turn allowed to react with benzaldehyde in the presence of a base, for example sodium ethoxide in absolute ethanol, to yield 1-methyl-5-nitro-2-styrylimidazole.

The next step in the synthesis is the oxidation of the styryl linkage of 1-methyl-5-nitro-2-styrylimidazole. This oxidation can be accomplished by any one of a number of oxidants suitable for oxidizing this type of linkage to the aldehyde (formyl) group.

According to one process, the oxidation can be accomplished by treating the 1-methyl-5-nitro-2-styrylimidazole, suspended in a suitable solvent, with ozone, at about room temperature. Suitable solvents include methanol, methanol and water mixture, or a mixture of methanol, methylene dichloride, and water, and the like.

Another method for oxidizing the styryl compound is taught by Henry et al., U.S. Pat. No. 3,472,864 (October 14, 1969). These authors teach the use of an oxidizing system comprising an alkali meal periodate and osmium tetroxide in a suitable aqueous solvent medium, preferably water and 1,2-dimethyloxyethane, at a temperature of from about 20° to 35° C., for a period of about 10 to 20 hours.

The next step in the preparation of the compound involves allowing the 1-methyl-5-nitroimidazole-2-carboxaldehyde, prepared as described supra, to react with a substituted hydrazine of the formula H$_2$N—NHR, wherein R represents C$_1$–C$_3$ alkyl or hydroxy (C$_1$–C$_3$)alkyl. The reaction is carried out in a suitable solvent such as chloroform, at reflux temperature, to yield a 1-methyl-5-nitroimidazole2-carboxaldehyde alkyl or substituted-alkyl hydrazone. Suitable substituted hydrazines for use in this reaction include methyl hydrazine, ethyl hydrazine, n-propyl hydrazine, isopropyl hydrazine, 2-hydroxyethyl hydrazine, and the like. The reaction conditions are the same for any one of the hydrazines. Thus, for example, when methyl hydrazine is allowed to react with 1-methyl-5-nitroimidazole-2-carboxaldehyde in chloroform solvent, there is obtained 1-methyl-5-nitroimidazole-2-carboxaldehyde methyl hydrazone.

The hydrazone formed in this manner is in turn allowed to react with N-bromosuccinimide at about room temperature in a suitable solvent, such as chloroform, to yield 1-methyl-5-nitroimidazole-2-carbon bromide alk or substituted-alk hydrazone. The reaction with N-bromosuccinimide is applicable to any of the substituted hydrazones to yield the bromo-substituted hydrazones. As a specific example, when 1-methyl-5-nitroimidazole-2-carboxaldehyde methyl hydrazone is allowed to react with N-bromosuccinimide at room temperature in chloroform solvent, there is obtained 1-methyl-5-nitroimidazole-2-carbonyl bromide methyl hydrazone.

This bromo-substituted hydrazone is unstable and has vesicant and lachrimatory properties. It is therefore used immediately without isolation or extensive purification. The bromo-substituted hydrazone is suspended in a suitable solvent, for example absolute methanol, and malononitrile is added thereto. To the mixture thus formed is added triethylamine dissolved in absolute methanol, while the temperature of the reaction mixture is maintained at about 10°–20° C. by suitable cooling means. This reaction is slightly exothermic and some cooling is required to maintain the desired temperature. As the reaction proceeds, the initial yellow suspension dissolves and is replaced by another suspension during a period of about 1 to about 2 hours. The solid material in this second suspension is the desired product, and is filtered off, washed with methanol and then with water, and dried. For example, when 1-methyl-5-nitroimidazole-2-carbonyl bromide methyl hydrazone is used, this solid material is identified by elemental analyses and NMR spectrum as 5-amino-1-methyl-3-(1-methyl-5-nitro-2-imidazolyl)pyrazole-4-carbonitrile. The homologous 5-amino-1-(alkyl or hydroxyalkyl)-3-(1-methyl-5-nitro-2-imidazolyl)pyrazole-4-carbonitriles can be prepared from the corresponding bromo-substituted alkyl or hydroxyalkyl hydrazones by following the same general procedure for reaction with malononitrile.

The preparation of a 5-amino-1-(haloalkyl)-3-(1-methyl-5-nitro-2-imidazolyl)pyrazole-4-carbonitrile is accomplished by reacting the corresponding hydroxyalkyl compound with a halogenating agent such as phosphorus trichloride, phosphorus tribromide, phosphorus trifluoride, thionyl chloride and the like. Thus, 5-amino-1-($\beta$-hydroxyethyl)-3-(1-methyl-5-nitro-2-imidazolyl)pyrazole-4-carbonitrile, is allowed to react with thionyl chloride in an inert solvent such as benzene, in the presence of a small amount of dimethylformamide to yield 5-amino-1-($\beta$-chloroethyl)-3-(1-methyl-5-nitro-2-imidazolyl)pyrazole-4-carbonitrile.

The synthesis of one of the novel compounds of the generic formula above, which compound also serves as the starting material for some of the other novel compounds coming within the scope of the generic formula, is exemplified as follows.

A mixture of 5-amino-1-methyl-3-(1-methyl-5-nitro-2-imidazolyl)pyrazole-4-carbonitrile, triethamine, and ethyl acetate is cooled to about 0° C., and there is then added dropwise a quantity of ethyl oxalyl chloride. During the addition, the temperature of the reaction mixture is maintained at about 0° C. After the addition is complete, the reaction mixture is heated to refluxing for about 14 hours, and is then worked up by filtering the reaction mixture hot. The solid which remains on the filter is discarded and the filtrate is concentrated in vacuo to leave a sticky oil. This oil crystallizes upon addition of a suitable solvent such as commercial absolute ethanol. The solid is identified by elemental analyses and NMR spectrum as N-[4-cyano-1-methyl-3-(1-methyl-5-nitroimidazol-2yl-)pyrazol-5-yl]-oxamic acid, ethyl ester.

The synthesis of other compounds coming within the scope of the generic formula above is carried out following the same general procedure described in the preceding paragraph, and using phenylglyoxyloyl chloride, pyruvoyl chloride, and the like.

The synthesis of still other compounds coming within the scope of the generic formula above is carried out by allowing hydrazine or hydroxylamine to react with the N-[4-cyano-1-substituted-3-(1-methyl-5-nitroimidazol-2-yl)pyrazol-5-yl]oxamic acid, ethyl ester, in a suitable solvent to yield the semioxamazide or the N'-hydroxyoxamide, respectively.

The esters or other derivatives of oxamic acid, prepared as set forth above, are then used for the preparation of the salts of the compounds. The preparation of one of these salts can be illustrated in the following manner. One of the esters, for example, N-[4-cyano-1-methyl3-(1-methyl-5-nitroimidazol-2-yl)pyrazol-5-yl]oxamic acid, ethyl ester, is suspended in a suitable carbinol such as ethanol and there is added thereto an equivalent of an inorganic base such as sodium hydroxide, potassium hydroxide, lithium hydroxide, ammonium hydroxide, or the like. The mixture is stirred for a period of time, suitably about a half hour, and the solid is filtered off. This solid is refluxed with acetone to remove any starting acid ester. The product obtained is identified by NMR spectrum and elemental analyses and, when sodium hydroxide is used, the product is identified as N-[4-cyano-1-methyl-3-(1-methyl-5-nitroimidazol-2-yl)pyrazol-5-yl]oxamic acid, ethyl ester, sodium salt.

The following examples more fully illustrate the synthesis of the novel compounds of this invention. These examples are not intended to limit the scope of the invention in any way.

EXAMPLE 1

N-[4-Cyano-1-methyl-3-(1-methyl-5-nitroimidazol-2-yl)pyrazol5-yl]oxamic acid, ethyl ester To a stirred mixture of 4.94 g. (0.02 mole) of 5-amino-1-methyl-3-(1-methyl-5-nitro-2-imidazolyl)-pyrazole-4-carbonitrile, 2.0 g. (0.02 mole) of triethamine, and 100 ml. of ethyl acetate cooled to 0° C., there was added dropwise 9.0 g. of ethyl oxalyl chloride, while the temperature of the reaction mixture was maintained at about 0° C. The reaction mixture was refluxed overnight and was worked up by filtering it hot. The solid was discarded and the filtrate was concentrated in vacuo to leave a sticky oil which crystallized upon the addition of commercial absolute ethanol. The mixture was warmed and all material which would not dissolve in the ethanol was filtered off and the filtrate was cooled. The material which precipitated was filtered off; it weighed about 3.1 g. and had a melting point of about 177°–182° C. It was identified by elemental analyses and NMR spectrum as N-[4-cyano-1-methyl-3-(1-methyl-5-nitroimidazol-2-yl)pyrazol-5-yl]oxamic acid, ethyl ester.

| Analyses calculated for $C_{13}H_{13}N_7O_5$. | | |
|---|---|---|
| | Theoretical | Found |
| C | 44.96% | 44.74% |
| H | 3.77 | 3.79 |
| N | 28.23 | 27.98 |

EXAMPLE 2

N-[4-Cyano-1-methyl-3-(1-methyl-5-nitroimidazol-2-yl)pyrazol-5-yl]oxamic acid, ethyl ester, sodium salt A suspension of 5.1 g. of N-[4-cyano-1-methyl-3-(1-methyl-5-nitroimidazol-2-yl)pyrazol-5-yl]oxamic acid, ethyl ester, in 150 ml. of ethanol was prepared, and a solution of 0.6 g. of sodium hydroxide in 2–3 ml. of water was added thereto. The mixture was stirred for about 0.5 hour and the mixture was filtered. The solid which was collected was water soluble. To remove starting ester, the solid was refluxed five times in acetone and filtered off each time. Thin-layer chromatography of the thus treated solid still showed a trace of ester present, so the solid was refluxed one more time in acetone. The product obtained weighed about 3.5 g., and had a melting point of about 276°–279° C. The product was identified by NMR spectrum and elemental analyses as N-[4-cyano-1-methyl-3-(1-methyl-5-nitroimidazol-2-yl)pyrazol-5-yl]oxamic acid, ethyl ester, sodium salt, plus one-half mole of water of crystallization.

| Analyses calculated for $C_{13}H_{12}N_7O_5Na \cdot \tfrac{1}{2}H_2O$. | | |
|---|---|---|
| | Theoretical | Found |
| C | 41.27% | 41.06% |
| H | 3.44 | 3.44 |
| N | 25.93 | 25.93 |

EXAMPLE 3

N-[4-Cyano-1-methyl-3-(1-methyl-5-nitroimidazol-2-yl)pyrazol-5-yl]oxamic acid, ethyl ester, potassium salt A suspension of 0.85 g. of N-[4-cyano-1-methyl-3-(1-methyl-5-nitroimidazol-2-yl)pyrazol-5-yl]oxamic acid, ethyl ester was prepared in 25 ml. of commercial absolute ethanol, and there was added thereto a solution of 0.16 g. of potassium hydroxide (87% pure) in about 0.5 ml. of water. The reaction mixture was stirred at ambient room temperature for about 1 to 1.5 hours. The mixture was filtered and the solid which was collected was washed with some commercial absolute ethanol. The solid was then refluxed with acetone and collected again. The solid was then refluxed with acetone and collected again. The solid weighed about 0.8 g. and had a melting point of about 279°–281° C. The product was identified by NMR spectrum and elemental analyses as N-[4-cyano-1-methyl-3-(1-methyl-5-nitroimidazol-2-yl)pyrazol-5-yl]oxamic acid, ethyl ester, potassium salt.

| Analyses calculated for $C_{13}H_{12}N_7O_5K$. | | |
|---|---|---|
| | Theoretical | Found |
| C | 40.52% | 40.47% |
| H | 3.14 | 3.30 |
| N | 25.44 | 25.47 |

EXAMPLE 4

N-[4-Cyano-1-methyl-3-(1-methyl-5-nitroimidazol-2-yl)pyrazol-5-yl]oxamic acid, ethyl ester, ammonium salt To a suspension of 0.5 g. of N-[4-cyano-1-methyl-3-(1-methyl-5-nitroimidazol-2-yl)pyrazol-5-yl]oxamic acid, ethyl ester, in 25 ml. of ethanol, there were added with stirring, six drops of 28 percent ammonia in water. The mixture was stirred overnight at ambient room temperature. The reaction mixture was filtered and the solid which was collected was stirred for a few minutes in acetone at ambient room temperature and the solvent filtered off and discarded. The solid which was obtained weighed about 0.3 g. and had a melting point of about 175°–179° C. The solid was identified by NMR spectrum and elemental analyses as N-[4-cyano-1-methyl-3-(1-methyl-5-nitroimdiazol-2-yl)pyrazol-5-yl]oxamic acid, ethyl ester, ammonium salt.

| Analyses calculated for $C_{13}H_{12}N_7O_5NH_4$. | | |
|---|---|---|
| | Theoretical | Found |
| C | 42.86% | 42.59% |
| H | 4.43 | 4.46 |
| N | 30.76 | 30.59 |

EXAMPLE 5

N-[4-Cyano-1-methyl-3-(1-methyl-5-nitroimidazol-2-yl)pyrazol-5-yl]oxamic acid, eth ester, lithium salt A suspension of 0.86 g. of N-[4-cyano-1-methyl3-(1-methyl-5-nitroimidazol-2-yl)pyrazol-5-yl]oxamic acid, ethyl ester was prepared in 25 ml. of commercial absolute ethanol, and there was added thereto, with stirring, 0.62 ml. of aqueous 4 molar lithium hydroxide solution. The solid material of the suspension went into solution almost immediately and the reaction mixture was stirred at ambient room temperature for about 4 hours. No precipitate formed. A considerable amount of ether was added to the solution and then the mixture was placed in the freezer over the weekend. A precipitate formed which was filtered off. The product thus obtained weighed about 0.28 g. and had a melting point of about 277°–288° C. The product was an orange pellet-like solid, and was identified by elemental analyses and NMR spectrum as N-[4-cyano-1-methyl-3-(1-methyl-5-nitroimidazol-2-yl)pyrazol-5-yl]oxamic acid, ethyl ester, lithium salt.

| Analyses calculated for $C_{13}H_{12}N_7O_5Li$. | | |
|---|---|---|
| | Theoretical | Found |
| C | 44.21% | 43.96% |
| H | 3.40 | 3.67 |
| N | 27.77 | 27.46 |

EXAMPLE 6

5-[4-Cyano-1-methyl-3-(1-methyl-5-nitroimidazol-2-yl)pyrazol5-yl]semioxamazide

A mixture of 1.73 g. of N-[4-cyano-13-(1-methyl-5-nitroimidazol-2-yl)pyrazol-5-yl]oxamic acid, ethyl ester, and 0.19 g. of anhydrous hydrazine in 50 ml. of ethanol was refluxed overnight. The solid was filtered off. It weighed about 0.87 g. and had a melting point of about 267°–273° C. The solid was identified by elemental analyses and NMR spectrum as 5-[4-cyano-1-methyl-3-(1-methyl-5-nitroimidazol-2-yl)pyrazol-5-yl]semioxamazide.

| Analyses calculated for $C_{11}H_{11}N_9O_4$. | | |
|---|---|---|
| | Theoretical | Found |
| C | 39.64% | 39.68% |
| H | 3.33 | 3.31 |
| N | 37.83 | 38.05 |

EXAMPLE 7

5-[4-Cyano-1-methyl-3-(1-methyl-5-nitroimidazol-2-yl)pyrazol-2-yl]semioxamazide, ammonium salt To a suspension of 0.5 g. of 5-[4-cyano-1-methyl-3-(1-methyl-5-nitroimidazol-2-yl)pyrazol-5-yl)semioxamazide in 25 ml. of commercial absolute ethanol, there was added, with sitrring, 6 to 8 drops of 28 percent aqueous ammonia. The material of the suspension went into solution, and within minutes a precipitate formed. The mixture was stirred from about 2 hours at ambient room temperature. The reaction mixture was filtered and the solid was collected. No attempt was made at recrystallization, since ammonia is lost thereby in heating, and starting material is isolated. There was obtained 0.25 g. of product having a melting point of about 253°–257° C. The product was identified by NMR spectrum as 5-[4-cyano-1-methyl-3-(1-methyl-5-nitroimidazol-2yl)pyrazol-5-yl]semioxamazide, ammonium salt.

EXAMPLE 8

5-[4-Cyano-1-methyl-3-(1-methyl-5-nitroimidazol-2yl)pyrazol-5-yl]semioxamazide, sodium salt To a suspension of 0.34 g. of 5-[4-cyano-1-methyl-3-(1-methyl-5-nitroimidazol-2-yl)pyrazol-5-yl]semioxamazide in 25 ml. of methanol, there was added a solution of about 0.1 g. of sodium hydroxide in about 1 ml. of water. The reaction mixture was stirred at ambient room temperature for about 5 hours. The reaction product mixture was filtered. The solid which was filtered off weighed about 0.43 g. and had a melting point of about 290°–293° C. The solid was identified by NMR spectrum and elemental analyses as 5-[4-cyano-1-methyl-3-(1-methyl-5-nitroimidazol-2-yl)pyrazol-5-yl]semioxamazide, sodium salt.

| Analyses calculated for $C_{11}H_{10}N_9O_4Na$. | | |
|---|---|---|
| | Theoretical | Found |
| C | 37.19% | 37.23% |
| H | 2.84 | 2.94 |
| N | 35.49 | 35.56 |

EXAMPLE 9

N-[4-Cyano-1-methyl-3-(1-methyl-5-nitroimidazol-2yl)pyrazol-5-yl]-N'-hydroxyoxamide Separate solutions were prepared of 0.94 g. of hydroxylamine hydrochloride in 10 ml. of methanol, and 0.728 g. of potassium hydroxide in 5 ml. of methanol at the boiling point of methanol. Both solutions were then cooled to about 30°–40° C., and the potassium hydroxide solution was added with shaking to the hydroxylamine hydrochloride solution. After the addition, the flask containing the mixture was flushed with nitrogen so that the mixture was maintained in a nitrogen atmosphere while being cooled in an ice bath for about 5 minutes to insure complete precipitation of the potassium chloride. The potassium chlordie was filtered off and the filtrate diluted with about 50 ml. of methanol. To this methanolic solution, there was then added 2.3 g. (0.0067 mole) of N-[4-cyano-1-methyl-3-(1-methyl-5-nitroimidazol-2-yl)pyrazol-5-yl]oxamic acid, ethyl ester, and the mixture was stirred for about 3 hours at ambient room temperature. A precipitate formed which was filtered off. The solid so collected was refluxed in methanol and the solid which did not dissolve was collected on a filter. The solid weighed about 0.3 g. and had a melting point of about 179°–180° C. The solid was identified by NMR spectrum and elemental analyses as N-[4-cyano-1-methyl-3-(1-methyl-5-nitroimidazol-2-yl)pyrazol-5-yl]-N'-hydroxyoxamide.

| Analyses calculated for $C_{11}H_{10}N_8O_5$. | | |
|---|---|---|
| | Theoretical | Found |
| C | 39.53% | 39.30% |
| H | 3.02 | 2.89 |
| N | 33.52 | 33.78 |

EXAMPLE 10

N-[4-cyano-1-methyl-3-(1-methyl-5-nitroimidazol-2-yl)pyrazol-5-yl]-2-phenylglyoxylamide The intermediate phenylglyoxyloyl chloride used in the preparation of the above-identified compound was synthesized in the following manner.

To 5.75 g. (0.038 mole) of phenylglyoxylic acid, there was added dropwise at room temperature 4.27 g. (0.037 mole) of α,α-dichloromethyl ether. During the addition the reaction mixture cooled down. After addition was complete, the solution was warmed for about 0.5 hour at about 50° C. The reaction product mixture was subjected to house vacuum for a few minutes on the rotary evaporator, and then the crude phenylglyoxyloyl choride was used immediately in the reaction which follows.

A mixture of 4.2 g. (0.017 mole) of 5-amino-1-methyl-3-(1-methyl-5-nitro-2-imidazolyl)pyrazole-4-carbonitrole, 150 ml. of ethyl acetate, and the crude phenylglyoxyloyl chloride prepared above (0.037 mole) was treated with 1.7 g. (0.017 mole) of triethylamine. The reaction mixture was refluxed overnight and then cooled. The solid which separated was filtered off, washed with considerable water, and recrystallized from dimethylformamide. There was obtained 4.4 g. of product having a melting point of about 225°–228° C. The product was identified by NMR spectrum and elemental analyses as N-[4-cyano-1-methyl-3(1methyl-5-nitroimidazol-2-yl)pyrazol-5yl]-2-phenylglyoxylamide.

| Analyses calculated for $C_{17}H_{13}N_7O_4$. | | |
|---|---|---|
| | Theoretical | Found |
| C | 53.83% | 54.03% |
| H | 3.45 | 3.66 |
| N | 25.85 | 25.93 |

EXAMPLE 11

N-[4-Cyano-1-methyl-3-(1-methyl-5-nitroimidazol-2-yl)pyrazol-5-yl]-2-phenylglyoxylamide, sodium salt A suspension of 1.0 g. (0.00264 mole) of N-[4-cyano-1-methyl-3-(1-methyl-5-nitroimidazol-2-yl)pyrazol-5-yl]-2-phenylglyoxylamide was prepared in 25 ml. of commercial absolute ethanol and there was added thereto a solution of 0.11 g. of sodium hydroxide in about 0.5 ml. of water. The original solid went into solution, and a precipitate quickly formed. After stirring for about 1 hour at ambient room temperature, the solid was filtered off and washed with commercial absolute ethanol. The solid weighed about 0.5 g. and had a melting point of about 309°–314° C. The solid was identified by NMR spectrum and elemental analyses as N-[4-cyano-1-methyl-3-(1-methyl-5-nitroimidazol-2-yl)pyrazol-5-yl]-2-phenylglyoxylamide, sodium salt, plus one mole of water of crystallization.

| Analyses calculated for $C_{17}H_{12}N_7O_4Na \cdot 1H_2O$ | | |
|---|---|---|
| | Theoretical | Found |
| C | 48.69% | 48.47% |
| H | 3.34 | 3.15 |
| N | 23.39 | 23.04 |

EXAMPLE 12

N-[4-Cyano-1-methyl-3-(1-methyl-5-nitroimidazol-2-yl)pyrazol-5-yl]-2-phenylglyoxylamide, ptoassium salt A suspension was prepared of 0.5 g. of N-[4-cyano-1-methyl-3-(1-methyl-5-nitroimidazol-2-yl)pyrazol-5-yl]-2-phenylglyoxylamide in about 25 ml. of commercial absolute ethanol, and there was added thereto with stirring a solution of 0.1 g. of potassium hydroxide in about 0.5 ml. of water. A precipitate formed in a few minutes and the mixture was stirred at ambient room temperature for about 2 hours. The reaction product mixture was filtered and the solid which was collected on the filter was washed with commercial absolute ethanol. The solid weighed about 0.35 g. and had a melting point of about 306°–313° C. The solid was recrystallized from commercial absolute ethanol and there was obtained 0.2 g. of product having a melting point of about 308°–312° C. It was identified by NMR spectrum and elemental analyses as N-[4-cyano-1-methyl-3-methyl-3-(1-methyl-5-nitroimidazol-2-yl)pyrazol-5-yl]-2-phenylglyoxylamide, potassium salt.

| Analyses calculated for $C_{17}H_{12}N_7O_4K$. | | |
|---|---|---|
| | Theoretical | Found |
| C | 48.92% | 48.77% |
| H | 2.90 | 2.92 |
| N | 23.49 | 23.25 |

EXAMPLE 13

N-[4-Cyano-1-methyl-3-(1-methyl-5-notroimidazol-2-yl)pyrazol-5-yl]pyruvamide

The pyruvoyl chloride used to synthesize the above-identified compound was prepared in the following manner.

To 3.3 g. (0.0375 mole) of pyruvic acid, there was added dropwise at room temperature with stirring 4.25 g. (0.0375 mole) of α,α-dichloromethyl ether and then the reaction mixture was warmed to about 50°. for about 0.5 hour. The reaction mixture was used without further purification in the reaction which follows.

To a mixture of 2.47 g. (0.01 mole) of 5-amino-1-methyl-3-(1-methyl-5-nitro-2-imidazolyl)pyrazole-4-carbonitrile, the crude pyruvo chloride prepared above, and 150 ml. of ethyl acetate, there was added dropwise 1.0 g. of triethylamine, and the reaction mixture refluxed for about 3 days. At the end of that time, the solid was filtered off and washed with water. This solid was identified by NMR spectrum and elemental analyses as N-[4-cyano-1-methyl-3-(1-methyl-5-nitroimidazol-2-yl)pyrazol-5-yl]pyruvamide.

| Analyses calculated for $C_{12}H_{11}N_7O_4$. | | |
|---|---|---|
| | Theoretical | Found |
| C | 45.43% | 45.51% |
| H | 3.49 | 3.63 |
| N | 30.90 | 30.71 |

The antimicrobial activity of the novel compounds of this invention has been demonstrated in several tests, as described hereinafter.

Experiment 1

The susceptibility of anaerobic bacteria, both gram positive and gram negative, to a representative number of the novel compounds of this application was determined using the agar dilution method. The bacteria used were isolated from patients hospitalized at the Indiana Univerisity Medical Center. The isolates were identified in the anaerobe laboratory of the Medical Center by the criteria established by Dowell et al., *Laboratory Methods in Anaerobic Bacteriology*. Public Health Serv. Publ. NO. 1803 (1968) [Center for Disease Control, Atlanta, Ga.]; and by Smith et al., *The Pathogenic Anaerobic Bacteria*, pages 96 –136 (1968) [Charles C. Thomas, Publisher, Springfield, Ill.]. All the organisms were maintained in chopped meat glucose medium (Scott Labs) at room temperature.

The method used for the agar dilution tests was based on the studies of Sutter et al., *Antimicrob. Ag. Chemother.* 3, 188–193 (1973). The strains of anaerobic bacteria were grown in 16 × 120 mm. tubes for 16 to 18 hours in Thioglycolate medium without indicator —135C (Becton, Dickinson and Co.), to which was added 5 mcg. of hemin per milliliter prior to autoclaving, plus 1 mg. of sodium bicarbonate and 0.1 of filter-sterilized menadione per milliliter after autoclaving. The strains were adjusted to the turbidity of the No. 1 McFarland standard in Thioglycolate medium without indicator —135C containing an additional 0.13 percent Bacto-agar (Difco). Each strain was then applied to the surface of the petri plate (100 × 15 mm.) by means of a replicator.

For the agar dilution studies, two-fold dilutions of the test compounds were prepared in deionized water to which was then added laked sheep blood and filter-sterilized menadione so the concentrations after the agar dilution were 5 percent and 10 mcg./ml. respectively. An equal volume of double strength Brucella agar (Becton, Dickinson and Co.) was mixed with each dilution in a water bath held at 50° C. and then poured onto the petri dishes.

All of the procedures were done inside a plastic glove box, except for the incubation of the growth tubes and the pouring of the plates. After the plates hardened, they were put inside the glove box for a minimum of 2 hours before they were inoculated. Generally, the glove box procedures of Aranki et al., *Applied Microbiology* 17, 568–576 (1969), were followed, but the following modifications were used. Dry materials were introduced into the glove box by evacuating the lock to 28 inches of mercury and filling once with nitrogen gas, followed by evacuating in the same manner and filling with an 80 percent nitrogen plus 10 percent $CO_2$ plus 10 percent hydrogen gas mixture. Liquid media and agar plates were introduced into the glove box by evacuating the lock to 10 inches of mercury and filling with gas four times. The nitrogen gas was used to fill the lock for the first two cycles of evacuation, with the gas mixture described above used for the final two fillings.

All the plates were incubated at 37° C. in Gas Pak jars (Becton, Dickinson and Co.) containing palladium-coated alumina catalysts (reactivated after each use). The results of the agar dilution tests were read after about 24 hours of incubation. The minimum inhibitory concentration (MIC) was recorded as the lowest concentration of test compound at which there was no growth.

The results of these in vitro tests are recorded in Chart 1, which follows. The test compounds are identified by the number of the example describing their preparation. The antibiotics clindamycin (C), and erythromycin (E) were also run simultaneously with the novel compounds of this application, for comparison purposes, and the results are included in Chart 1 below.

Chart 1

| Anaerobic Bacteria | SUSCEPTIBILITY OF ANAEROBIC BACTERIAL ISOLATES 24 Hr. MIC (mcg./ml.) Compound of Example No. | | | | | | | | | |
|---|---|---|---|---|---|---|---|---|---|---|
| | 1 | 2 | 3 | 4 | 6 | 8 | 10 | 11 | C | E |
| *Bacteroides fragilis* sp. fragilis 1877 | 0.25 | 0.5 | 0.25 | | 0.5 | | ≦0.03 | 0.06 | 0.25 | 2 |
| *Bacteroides fragilis* sp. fragilis 103 | ≦0.03 | 0.125 | 0.125 | | 0.06 | | ≦0.03 | 0.06 | ≦0.06 | 4 |
| *Bacteroides fragilis* sp. fragilis 104 | 0.25 | 0.25 | 0.25 | | 0.25 | | ≦0.03 | ≦0.03 | 0.125 | 2 |
| *Bacteroides fragilis* sp. fragilis 106 | 0.125 | 0.25 | 0.25 | | 0.25 | | ≦0.03 | ≦0.03 | 0.125 | 4 |
| *Bacteroides fragilis* sp. fragilis 107 | 0.25 | 0.25 | 0.25 | | 0.5 | | ≦0.03 | 0.06 | 0.25 | 2 |
| *Bacteroides fragilis* sp. fragilis 108 | 0.125 | 0.25 | 0.25 | | 0.5 | | ≦0.03 | 0.06 | 0.125 | 2 |
| *Bacteroides fragilis* sp. fragilis 110 | 0.25 | 0.25 | 0.5 | | 0.5 | | ≦0.03 | 0.06 | 0.125 | 16 |
| *Bacteroides fragilis* sp. fragilis 111 | 0.125 | 0.25 | 0.25 | | 0.25 | | ≦0.03 | 0.06 | 1.0 | 2 |
| *Bacteroides fragilis* sp. fragilis 112 | 0.125 | 0.25 | 0.25 | | 0.5 | | ≦0.03 | 0.06 | 0.25 | 32 |
| *Bacteroides fragilis* sp. fragilis 113 | 0.25 | 0.25 | 0.5 | | 0.25 | | ≦0.03 | 0.125 | 0.125 | 2 |
| *Bacteroides fragilis* sp. fragilis 1451 | 0.25 | 0.25 | 0.25 | | 0.5 | | ≦0.03 | 0.125 | 1.0 | 0.5 |
| *Bacteroides fragilis* sp. fragilis 1470 | 0.125 | 0.25 | 0.25 | | 0.25 | | ≦0.03 | 0.06 | 0.25 | 8 |
| *Bacteroides fragilis* sp. fragilis 2 | 0.25 | 0.25 | 0.25 | | 0.25 | | ≦0.03 | 0.06 | 0.25 | 4 |
| *Bacteroides fragilis* sp. fragilis 9 | 0.25 | 0.5 | 0.25 | | 0.25 | | ≦0.03 | 0.06 | 0.125 | 4 |
| *Bacteroides fragilis* sp. fragilis 62 | 0.25 | 0.125 | 0.5 | | 0.5 | | ≦0.03 | 0.06 | 0.25 | 8 |
| *Bacteroides fragilis* sp. fragilis 1874 | 0.06 | 0.25 | 0.25 | | 0.25 | | ≦0.03 | ≦0.03 | ≦0.06 | 0.5 |
| *Bacteroides fragilis* | | | | | | | | | | |

Chart 1-continued

SUSCEPTIBILITY OF ANAEROBIC BACTERIAL ISOLATES
24 Hr. MIC (mcg./ml.)

| Anaerobic Bacteria | Compound of Example No. | | | | | | | | | |
|---|---|---|---|---|---|---|---|---|---|---|
| | 1 | 2 | 3 | 4 | 6 | 8 | 10 | 11 | C | E |
| sp. vulgatis 1563 | 0.125 | 0.5 | 0.25 | | 0.125 | | 0.06 | 0.25 | 0.125 | 1.0 |
| Bacteroides fragilis sp. thetaiotaomicron 1438 | 0.25 | 0.25 | 0.5 | | 1.0 | | ≤0.03 | 0.125 | 0.5 | 1.0 |
| Bacteroides fragilis sp. thetaiotaomicron 1900A | 0.25 | 0.25 | 0.5 | | 0.25 | | ≤0.03 | 0.125 | 4 | >64 |
| Actinomyces israelii W855 | >64 | >64 | | >128 | >64 | >128 | >64 | >64 | ≤0.5 | ≤0.5 |
| Clostridium perfringens 81 | 0.5 | ≤0.25 | | ≤0.5 | 0.5 | 2 | 1.0 | 0.5 | 4 | 1.0 |
| Clostridium septicum 1128 | >128 | >64 | | 16 | >128 | >128 | 1.0 | 0.25 | 8 | 1.0 |
| Eubacterium aerofaciens 1235 | 0.5 | ≤0.25 | | ≤0.5 | 0.5 | 4 | 2 | 0.5 | 8 | ≤0.5 |
| Peptococcus asaccharolyticus 1302 | 1.0 | ≤0.25 | | ≤0.5 | ≤0.25 | 1.0 | 1.0 | 1.0 | ≤0.5 | 1 |
| Peptococcus prevoti 1281 | ≤0.25 | 0.5 | | 32 | 0.5 | 32 | 16 | 2 | 32 | >128 |
| Peptostreptococcus anaerobius 1428 | ≤0.25 | ≤0.25 | | ≤0.5 | ≤0.25 | 0.5 | 1.0 | 0.25 | ≤0.5 | ≤0.5 |
| Peptostreptococcus intermedius 1264 | 16 | >64 | | ≤0.5 | 32 | 32 | 64 | 32 | 1.0 | ≤0.5 |
| Propionibacterium acnes 79 | 32 | >64 | | >128 | 32 | >128 | 64 | 64 | ≤0.5 | ≤0.5 |
| Bacteroides fragilis sp. fragilis 1936B | ≤0.25 | ≤0.25 | | ≤0.5 | ≤0.25 | 1.0 | 2 | 0.06 | ≤0.5 | 2 |
| Bacteroides melaninogenicus 1856/28 | 16 | 16 | | 1.0 | 8 | 16 | 32 | 16 | ≤0.5 | 4 |
| Bacteroides melaninogenicus 2736 | ≤0.25 | 0.5 | | ≤0.5 | ≤0.25 | 0.5 | 2 | ≤0.03 | ≤0.5 | 1.0 |
| Bacteroides vulgatis 1211 | ≤0.25 | ≤0.25 | | ≤0.5 | ≤0.25 | 1.0 | 4 | 1.0 | ≤0.5 | 1.0 |
| Bacteroides corrodens 1874 | ≤0.25 | ≤0.25 | | ≤0.5 | ≤0.25 | 1.0 | 1.0 | 0.25 | ≤0.5 | ≤0.5 |
| Fusobacterium symbiosum 1470 | ≤0.25 | ≤0.25 | | ≤0.5 | ≤0.25 | 0.5 | ≤0.03 | ≤0.03 | ≤0.5 | ≤0.5 |
| Fusobacterium necrophorum 6054A | ≤0.25 | ≤0.25 | | ≤0.5 | ≤0.25 | 0.5 | 0.5 | 0.25 | ≤0.5 | 8 |

Experiment 2

The efficacy of the novel compounds in the control of infections caused by *Salmonella typhimurium* in chickens was evaluated in the following manner.

The test was carried out using day-old chicks weighing approximately 35 g. each. The chicks were divided into groups of 5 chicks per each dosage level. A portion of the chicks received the test compound which was suspended in 0.2 ml. of polyethylene glycol 200 and administered subcutaneously in the neck. A control group of chicks did not receive the compound. All the chicks were challenged with a 1:200 dilution of a culture of the organism, 0.1 ml. of the dilution being injected into each chick in the leg intramuscularly. The chicks were observed for 6 days; the number of deaths occurring in the control group was compared with the number of deaths occurring in the chicks which received the test compound. The results are set forth in Chart 2, which follows. The test compounds are identified in the same manner as set forth in experiment 1.

In the chart, column 1 lists the compounds tested; column 2, the dosage of test compound in mg./kg.; and column 3, the survival ratio.

Chart 2

| Compound | Dosage mg./kg. | Survival Ratio |
|---|---|---|
| 1 | 60 | 4/5 |
| 2 | 60 | 2/5 |
| 3 | 60 | 3/5 |
| 6 | 60 | 5/5 |
| 9 | 60 | 4/5 |

The results of the tests indicate the novel compounds are active in vitro against a number of anaerobic bacteria, and some compounds are also active in vivo against *Salmonella typhimurium* in chicks.

I claim:

1. A compound selected from the group consisting of

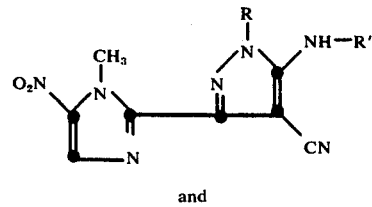

and

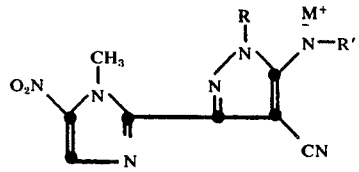

wherein
R is methyl;
R' is selected from the group consisting of

and

M is an ion selected from the group consisting of Na$^+$ and K$^+$.

2. A compound as in claim 1, said compound being N-[4-cyano-1-methyl-3-(1-methyl-5-nitroimidazol-2-yl)pyrazol-5-yl]oxamic acid, ethyl ester, potassium salt.

3. A compound as in claim 1, said compound being N-[4-cyano-1-methyl-3-(1-methyl-5-nitroimidazol-2-yl)pyrazol-5-yl]oxamic acid, ethyl ester, sodium salt.

4. A compound as in claim 1, said compound being N-[4-cyano-1-methyl-3-(1-methyl-5-nitroimidazol-2-yl)pyrazol-5-yl]-N'-hydroxyoxamide.

5. A compound as in claim 1, said compound being N-[4-cyano-1-methyl-3-(1-methyl-5-nitroimidazol-2-yl)pyrazol-5-yl)oxamic acid, ethyl ester.

6. A compound as in claim 1, said compound being 5-[4-cyano-1-1-methyl-3-(1-methyl-5-nitroimidazol-2-yl)pyrazol-5-yl]semioxamazide.

* * * * *

UNITED STATES PATENT OFFICE
CERTIFICATE OF CORRECTION

Patent No. 4,029,671                    Dated June 14, 1977

Inventor(s) Henry Friedman; Emily J. Canada

It is certified that error appears in the above-identified patent and that said Letters Patent are hereby corrected as shown below:

Column 1, line 57:  "$\underline{M}+$" should read --$\underline{M}\oplus$--.

Column 2, line 23:  "$\underline{M}+$" should read --$\underline{M}\oplus$--.

Column 3, line 31:  "meal" should read --metal--.

Column 3, line 43:  "nitroimidazole2" should read --nitroimidazole-2--.

Column 3, line 57:  "carbon" should read --carbonyl--.

Column 3, line 58:  "alk or substituted-alk" should read --alkyl or substituted-alkyl--.

Column 4, line 62:  "using phenylglyoxyloyl" should read --using other suitable and desirable acid chlorides such as phenylglyoxyloyl--.

Column 5, line 8:   "methyl3" should read --methyl-3--.

Column 5, line 29:  "yl)pyrazol5" should read --yl)pyrazol-5--.

Column 5, line 32:  "trietha-" should read --triethyla---.

Column 7, line 11:  "eth" should read --ethyl--.

Column 7, line 12:  "methyl3" should read --methyl-3--.

Column 7, line 43:  "[4-cyano-13-(1-methyl-5-" should read --[4-cyano-1-methyl-3-(1-methyl-5---.

Column 7, line 67:  "sitrring" should read --stirring--.

UNITED STATES PATENT OFFICE
CERTIFICATE OF CORRECTION

Patent No. 4,029,671                    Dated   June 14, 1977

Inventor(s) Henry Friedman; Emily J. Canada

It is certified that error appears in the above-identified patent and that said Letters Patent are hereby corrected as shown below:

Column 8, line 2 :   "from" should read --for--.

Column 8, line 10:   "2yl" should read --2-yl--.

Column 8, line 15:   "2yl" should read --2-yl--.

Column 8, line 41:   "2yl" should read --2-yl--.

Column 8, line 54:   "potassium chlordie" should read --potassium chloride--.

Column 9, line 38:   "(1methyl-" should read --(1-methyl---.

Column 10, line 29:  "methyl-3-methyl-3-(1-methyl" should read --methyl-3-(1-methyl--.

Column 10, line 41:  "notroimidazol" should read --nitroimidazol--.

Column 10, line 54:  "pyruvo" should read --pyruvoyl--.

Column 13, line 39:  "typhimuriumin" should read --_typhimurium_ in--.

UNITED STATES PATENT OFFICE
CERTIFICATE OF CORRECTION

Patent No. 4,029,671     Dated June 14, 1977

Inventor(s) Henry Friedman; Emily J. Canada

It is certified that error appears in the above-identified patent and that said Letters Patent are hereby corrected as shown below:

Column 14, line 53: "$\underline{M}+$" should read --$\underline{M}\oplus$--.

Column 16, line 8: "$\underline{/}$4-cyano-1-1-methyl" should read --$\underline{/}$4-cyano-1-methyl--.

Signed and Sealed this

First Day of November 1977

[SEAL]

Attest:

RUTH C. MASON  
Attesting Officer

LUTRELLE F. PARKER  
Acting Commissioner of Patents and Trademarks